United States Patent
Chang et al.

(10) Patent No.: US 9,950,297 B2
(45) Date of Patent: Apr. 24, 2018

(54) METHOD FOR CONCENTRATING AQUEOUS CONTAINING SOLUTE INTO HIGH CONCENTRATION BY HYDRAULIC-MEMBRANE PROCESS UNDER NO DIFFERENCE IN OSMOTIC PRESSURE

(71) Applicant: KOREA ADVANCED INSTITUTE OF SCIENCE AND TECHNOLOGY, Daejeon (KR)

(72) Inventors: Ho Nam Chang, Daejeon (KR); Kwonsu Jung, Gwangju (KR); Gwon Woo Park, Jeollanam-do (KR); Yeu-Chun Kim, Daejeon (KR); Charles Seo, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 247 days.

(21) Appl. No.: 14/764,975

(22) PCT Filed: Feb. 4, 2014

(86) PCT No.: PCT/KR2014/000952
§ 371 (c)(1),
(2) Date: Jul. 30, 2015

(87) PCT Pub. No.: WO2014/123339
PCT Pub. Date: Aug. 14, 2014

(65) Prior Publication Data
US 2015/0367285 A1  Dec. 24, 2015

(30) Foreign Application Priority Data

Feb. 6, 2013  (KR) .................. 10-2013-0013558

(51) Int. Cl.
*B01D 61/00* (2006.01)
*B01D 61/02* (2006.01)
(Continued)

(52) U.S. Cl.
CPC ......... *B01D 61/002* (2013.01); *B01D 61/022* (2013.01); *B01D 61/025* (2013.01);
(Continued)

(58) Field of Classification Search
CPC .... B01D 61/002; B01D 61/025; B01D 61/58; B01D 61/022; B01D 61/06; B01D 61/08;
(Continued)

(56) References Cited

U.S. PATENT DOCUMENTS 6,849,184 B1 * 2/2005 Lampi ................. B01D 61/002
                                                210/321.72
2006/0144789 A1 * 7/2006 Cath ................... B01D 61/002
                                                210/641
(Continued)

FOREIGN PATENT DOCUMENTS

KR   10-2011-0081518 A   7/2011
KR   10-2012-0050897 A   5/2012
(Continued)

OTHER PUBLICATIONS

Butler, E.L. (May 6, 2012). Point of use water treatment with forward osmosis for emergency and population migration relief. Honors Scholar Theses. http://digitalcommons.uconn.edu/srhonors_theses/279.*

(Continued)

*Primary Examiner* — Katherine Zalasky
*Assistant Examiner* — Benjamin Lebron
(74) *Attorney, Agent, or Firm* — HULTQUIST, PLLC; Steven J. Hultquist

(57) ABSTRACT

The present invention relates to a method of concentrating an aqueous solution at low pressure under a zero osmotic (Continued)

pressure difference condition, and more particularly, to a method of concentrating an aqueous solution containing a solute to be concentrated, at low pressure under a zero osmotic pressure difference condition. The method of the present invention comprises the steps of: (a) discharging water of a solute-containing aqueous solution to be concentrated, from a reverse osmosis separator to the outside, and transferring the concentrated aqueous solution to a zero osmotic pressure difference concentrator; (b) further concentrating the concentrated aqueous solution using the zero osmotic pressure difference concentrator comprising a feed chamber and a draw chamber, which are separated from each other by a reverse osmosis membrane or a forward osmosis membrane; and (c) recovering the solute and water from the aqueous solution further concentrated in the zero osmotic pressure difference concentrator. When the method of concentrating the aqueous solution at low pressure under the zero osmotic pressure difference condition is used, the aqueous solution can be concentrated to the maximum saturation concentration of a solute or a solution concentration of 100% using a reduced amount of energy without having to use an extraction solvent. In addition, there is an advantage in that a separate osmosis draw solution does not need to be used.

7 Claims, 6 Drawing Sheets

(51) Int. Cl.
*B01D 61/08* (2006.01)
*C12M 1/00* (2006.01)
*C07C 29/76* (2006.01)
*C07C 51/47* (2006.01)
*C01D 3/04* (2006.01)
*C07C 31/08* (2006.01)
*C07C 69/02* (2006.01)
*B01D 61/58* (2006.01)
*C02F 1/44* (2006.01)
*B01D 63/10* (2006.01)
*B01D 63/12* (2006.01)
*B01D 61/06* (2006.01)
*C02F 101/32* (2006.01)
*C02F 103/08* (2006.01)

(52) U.S. Cl.
CPC .............. *B01D 61/06* (2013.01); *B01D 61/08* (2013.01); *B01D 61/58* (2013.01); *B01D 63/10* (2013.01); *B01D 63/12* (2013.01); *C01D 3/04* (2013.01); *C02F 1/441* (2013.01); *C02F 1/445* (2013.01); *C07C 29/76* (2013.01); *C07C 31/08* (2013.01); *C07C 51/47* (2013.01); *C07C 69/02* (2013.01); *C12M 47/10* (2013.01); *B01D 2311/2669* (2013.01); *B01D 2315/14* (2013.01); *B01D 2317/08* (2013.01); *C02F 2101/322* (2013.01); *C02F 2103/08* (2013.01)

(58) Field of Classification Search
CPC .... B01D 2315/14; B01D 63/10; B01D 63/12; B01D 2311/2669; B01D 2317/08; C01D 3/04; C02F 1/441; C02F 1/445; C02F 2101/322; C02F 2103/08; C07C 31/08; C07C 29/76; C07C 51/47; C07C 69/02; C12M 47/10

See application file for complete search history.

(56) References Cited

U.S. PATENT DOCUMENTS

| 2012/0118826 A1 | 5/2012 | Liberman et al. |
| 2012/0118827 A1 | 5/2012 | Chang et al. |
| 2012/0267307 A1 | 10/2012 | McGinnis |
| 2012/0267308 A1 | 10/2012 | Carmignani et al. |

FOREIGN PATENT DOCUMENTS

| KR | 10-1229482 B1 | 2/2013 |
| WO | 2011084002 A2 | 7/2011 |

OTHER PUBLICATIONS

Choi, Y.J., et al., "Toward a combined system of forward osmosis and reverse osmosis for seawater desalination," Desalination, 247, pp. 239-246 (2009).*
CSM, "A Division of Woongjin Chemical", (As Accessed via http://www.csmfilter.com on Jul. 30, 2015), 2009, p. 1.
Lachish, U., "Optimizing the Efficiency of Reverse Osmosis Seawater Desalination", (As Accessed via http://urila.tripod.com/Seawater.htm on Jul. 30, 2015), May 2002, pp. 1-19.
Lenntech BV, "Ionic Strength, activity coefficient and solubility calculator", (Jan. 20, 2014 version unavailable, As Accessed via http://www.lenntech.com/calculators/activity/activity-coefficient.htm on Jul. 29, 2015), Jan. 20, 2014, p. 1
Lewis, G., "The Osmotic Pressure of Concentrated Solutions, and the Laws of the Perfect Solution.", J. Am. Chem. Soc., May 1908, pp. 668-683, vol. 30, No. 5.
Loeb, S., "Production of Energy from Concentrated Brines by Pressure-Retarded Osmosis: I. Preliminary Technical and Economic Correlations", Journal of Membrane Science, Dec. 1976, pp. 49-63, vol. 1.
Loeb, S., "The Loeb-Sourirajan Membrane: How it Came About", "ACS Symposium Series vol. 153", Synthetic Membranes: vol. I: Desalination, May 21, 1981, pp. 1-9, Publisher: American Chemical Society, Published in: Washington, D.C.
McCutcheon, J., et al., "A novel ammonia-carbon dioxide forward (direct) osmosis desalination process", Desalination, May 13, 2005, pp. 1-11, vol. 174.
Wikipedia, "Multi-stage flash distillation", (As Accessed via http://en.wikipedia.org/wiki/Multi-stage_flash_distillation on Jul. 30, 2015), Jun. 18, 2015, pp. 1-3.

* cited by examiner $$C_4 = (1+P_4/q_4)C_3 \quad (1) \qquad C_6 = \frac{C_5}{(1+P_4/q_5)} = \frac{(1+P_4/q_4)}{(1+P_4/q_5)} C_3 \quad (2)$$

$$\text{concentration difference} = C_4 - C_6 = \frac{(1+P_4/q_4)}{(1+P_4/q_5)} (P_4/q_5) C_3 \quad (3)$$

$$\text{osmotic pressure difference} = \Pi(C_4) - \Pi(C_6) \approx (P_4/q_5) C_3 \quad (4)$$

given $P_4/q_4, P_4/q_5 << 1$ volume balance : $q_3 - P_4 = q_4$ (1), $q_4 + P_4 = q_6$ (2)

solute balance : $C_3 q_3 = C_4 q_4$ (3), $C_5 q_5 = C_6 q_6$ (4)

$$C_5 = (1+P_4/q_4) \quad (5), \qquad C_4 = C_5 \quad (6) \qquad C_6 = \frac{(1+P_4/q_4)}{(1+P_4/q_5)} C_3 \quad (7)$$

METHOD FOR CONCENTRATING AQUEOUS CONTAINING SOLUTE INTO HIGH CONCENTRATION BY HYDRAULIC-MEMBRANE PROCESS UNDER NO DIFFERENCE IN OSMOTIC PRESSURE

CROSS-REFERENCE TO RELATED APPLICATIONS

This application is a U.S. national phase under the provisions of 35 U.S.C. § 371 of International Patent Application No. PCT/KR14/00952 filed Feb. 4, 2014, which in turn claims priority of Korean Patent Application No. 10-2013-0013558 filed Feb. 6, 2013. The disclosures of such international patent application and Korean priority patent application are hereby incorporated herein by reference in their respective entireties, for all purposes.

TECHNICAL FIELD

The present invention relates to a method of concentrating an aqueous solution at low pressure under a zero osmotic pressure difference condition, and more particularly, to a method of concentrating an aqueous solution containing a solute to be concentrated, at low pressure under a zero osmotic pressure difference condition.

BACKGROUND ART

Materials that are needed by humans are present as solids, liquids and gases in the sea, land and air, and are also present as independent molecules or compounds. Desired materials can be obtained by catalytic reactions, chemical reactions, biological reactions, etc.

For example, salt that is most frequently used by humans is present in sea water at a concentration of 3.0 wt %. 1000 g of sea water consists of 30 g of salt and 970 g of water. If 500 g of water is removed therefrom, 30 g of salt and 470 g of water remain, and if 250 g of water is additionally removed, 220 g of water and 30 g of salt remain. If 125 g of water is further removed, 95 g of water and 30 g of salt (28%) remain. If 62.5 g is subsequently removed, 22.5 g of water and 30 g of salt remain, and in this case, the content of salt is 57.1 wt %. However, because the maximum solubility of salt is 26.4% (359 g/1000 g water), water is continually removed, but salt starts to precipitate as a crystal before 22.5 g of water and 30 g of salt are reached.

In the case of organic acids, when easily decomposable animal and vegetable materials such as food waste start to be anaerobically decomposed, polymers are converted into single molecules which then form mixtures of organic acids (acetic acid, propionic acid, butyric acid, etc.), resulting in methane gas and carbonic acid gas. Herein, the concentration of organic acids that can be obtained by fermentation is known to about 35 g/L (45 g/L, sodium salt). However, in order to use these organic acids as a raw material for biofuel (bioalcohol, biodiesel, etc.), an additional process for concentrating the organic acids is required. US Patent Publication No. 2012-0118827 discloses concentrating an organic acid about four times (140 g/L of solvent) using forward osmosis.

Methods of further concentrating a concentrated organic acid include a method in which a mixture of calcium and organic acid is prepared using calcium hydroxide (Ca(OH)$_2$), followed by heating. When this method is used, the organic can be concentrated to 100%, and when 98% sulfuric acid (H$_2$SO$_4$) is added thereto, calcium as calcium sulfate (CaSO$_4$) can be precipitated as a salt. Organic acids can be obtained by fermentation of organic matter, and particularly, an organic acid mixture comprising acetic acid, propionic acid and butyric acid at a ratio of 8:1:1 6:1:3 or 5:1:5 depending on a fermentation process and a raw material can be produced.

Bioethanol is produced as a solution containing 6-10% ethanol from maize starch, sugar canes, etc.

Metha (1982) concentrated a 7.6% ethanol-containing solution to 20-30% by reverse osmosis at 60 atm, concentrated the concentrated solution to 95% by distillation, concentrated the distilled solution to 99.5% by azeotropic distillation to obtain ethanol for fuel, and compared the economic efficiency of this method with that of a method that uses distillation from beginning (see Metha, G D, Journal of Membrane Science, 12, 1-26 (1982).

Energy required for the concentration of salt, volatile fatty acids (VFA) and ethanol in the above-described examples is shown in Table 1 below.

TABLE 1

| Material | Thermal method | Use of membrane | Reason for limit |
|---|---|---|---|
| Salt | Possible (up to 100%) | Up to 7% | Osmotic pressure of feed solution |
| VFA | Possible (up to 100%) | Up to 14% (forward osmosis) | Osmotic pressure of feed solution |
| Ethanol | Possible (up to 95%) | Possible only at low concentration (20-30%) | Osmotic pressure of feed solution |

Energy required to remove 1000 g of water by a thermal method is 730 kwh, because energy required to evaporate 1 m$^3$ of water at 30° C. to steam 100° C. is 2.7×10$^9$ joule and 1 kwh is 3.6×10$^6$ joule. Thermal energy can be used several times, and thus the multi-stage flash (MSF) process requires energy of about 25 kwh (http://en.wikipedia.org/wiki/Multi-Stage_Flash) accessed on Nov. 10, 2012).

Meanwhile, membrane processes (reverse osmosis and forward osmosis) requires energy of 2.5 mJ to remove 1 m$^3$ of water, and this amount of energy corresponds to 0.69 kwh (=2.5 mJ/3.6 mJ). The multi-stage flash (MSF) process having the highest efficiency among thermal processes requires energy of 25 kwh, whereas the use of membranes requires energy of 0.69 kwh, indicating that the application of the membrane process leads to an increase in economic efficiency (http://en.wikipedia.org/wiki/Multi-stage_flash_distillation).

Currently, the membrane process is applied not only to reverse osmosis, but also to forward osmosis, and thus is used in many industrial fields. In the membrane process, the flux of a solvent (water) and the movement of a solute (salt, VFA, ethanol, etc.) are as follows.

$$Jw = Lp(\Delta P - \sigma \Delta \pi) \quad (1)$$

$$Js = Cs(1-\sigma)Jw + \omega \Delta \pi \quad (2)$$

wherein Jw is water flux; Lp is water permeability coefficient; ΔP is the hydraulic pressure difference between a feed chamber and a draw chamber; Δπ is the osmotic pressure difference between the feed chamber and the draw chamber; and Js is the flux of the solute, which is divided into one caused by Jw and one caused by the osmotic pressure difference.

If Jw is not present in equation (2) above, the solute can move from the draw chamber to the feed chamber due to the osmotic pressure difference. σ is the reflection coefficient of the solute by the membrane, and at σ=1, the solute is completely impermeable, and the osmotic pressure difference between the two chambers reaches the maximum.

Osmotic pressure is expressed as the following equation (3):

$$\pi = CRT \quad (3)$$

wherein C is concentration; R is gas constant; and T is temperature.

In addition, the Lewis equation for a solution containing a high concentration of a solute is expressed as the following equation 4:

$$\pi = RT/v_{sp} \ln(1-\gamma X) \quad (4)$$

wherein Vsp is the volume of 1 mole of a solvent when the concentration of a solute is 0; γ is the activity coefficient of the solvent; and X is the molar fraction of the solute (References: Lewis, G. N., The osmotic pressure of concentrated solutions and the laws of perfect solution. *Journal of the American Chemical Society* 1908, 30, 668-683.).

If 30 g/L of a solute is dissolved in water, the osmotic pressure of the solute is 25.4 bar for salt, 0.01 bar for albumin, and $1.2 \times 10^{-12}$ bar for particles.

The reverse osmosis and reverse osmosis processes have an advantage in that energy is saved due to the use of membrane, but have a disadvantage in that, as concentration progresses, the osmotic pressure in the feed chamber increases so that it is impossible to further concentrate the feed solution or to increase the utility of the feed solution (Loeb, S, Loeb-Sourirajan Membrane, How it Came About Synthetic Membranes, ACS Symposium Series, 153, 1, 1~9, 1981; Loeb, S., J. Membr. Sci, 1, 49, 1976).

The forward osmosis process that recently started to be studied is a process in which a material having high osmotic pressure is used in the draw chamber so that only water will move from the feed chamber to the draw chamber due to Δπ rather than ΔP (McCutcheon J R, McGuinnis R L, Elimelech R L, Desalination, 174, 1~11, 2005).

The forward osmosis process has an advantage in that the osmotic pressure of the draw chamber is maximized. However, as the amount of water moving to the draw chamber increases, Δπ decreases gradually, and thus the amount of permeate decreases gradually. In this case, the draw solution can be regenerated, but this regeneration is not economic. In addition, there is a disadvantage in that, as the concentration of the draw solution in the draw chamber increases, the solute in the draw solution is diffused back into the feed chamber through the membrane.

Accordingly, the present inventors have made extensive efforts to solve the above-described problems, and as a result, have found that, when a solute-containing aqueous solution is introduced into the feed chamber of a concentrator comprising the feed chamber and a draw chamber, which are separated from each other by a reversal osmosis membrane and/or a forward osmosis membrane, and when a solution having the same osmotic pressure as that of the aqueous solution introduced into the feed chamber is introduced into the draw chamber, Δπ in equations (1) and (2) above can be eliminated or minimized so that the feed solution can be concentrated even by hydraulic pressure alone under a zero osmotic pressure difference condition (Δπ=0) or a low osmotic pressure difference condition, and for this reason, the diluted draw solution will have low osmotic pressure so that pure water can be recovered by reverse osmosis, and ultimately, energy consumption and management costs can be minimized while concentration of the feed solution can be maximized, thereby completing the present invention.

DISCLOSURE OF INVENTION

Technical Problem

It is an object of the present invention to a method for concentrating an aqueous solution, which can minimize energy and management costs while maximizing the concentration of an aqueous solution containing a variety of solutes to be concentrated.

Technical Solution

To achieve the above object, the present invention provides a method of concentrating an aqueous solution containing a solute to be concentrated, the method comprising the steps of: (a) firstly concentrating the solute-containing aqueous solution to be concentrated by reverse osmosis; (b) introducing the firstly concentrated solute-containing aqueous solution of step (a) into a zero osmotic pressure difference concentrator comprising a feed chamber and a draw chamber, which are separated from each other by a reverse osmosis membrane or a forward osmosis membrane, thereby secondly concentrating the introduced solute-containing aqueous solution in the concentrator; and (c) recovering the secondly concentrated solute-containing aqueous solution while recycling a portion of the secondly concentrated solute-containing aqueous solution to the draw chamber to form a zero osmotic pressure difference between the feed chamber and the draw chamber.

In the present invention, step (b) comprises the steps of: (i) transferring the firstly concentrated aqueous solution of step (a) to the feed chamber of the zero osmotic pressure difference concentrator, and introducing into the draw chamber either a solution having an osmotic pressure identical to that of the aqueous solution transferred to the feed chamber or a solution having an osmotic pressure in a range that does not influence ΔP in equation (1), thereby forming the zero osmotic pressure difference between the feed chamber and the draw chamber; and (ii) applying a pressure of 1-5 atm for the forward osmosis (FO) membrane or 5-200 atm for the reverse osmosis membrane to the feed chamber under the zero osmotic pressure difference condition to transfer water of the concentrated aqueous solution to the draw chamber, thereby secondly concentrating the concentrated aqueous solution.

The method of concentrating the aqueous solution at low pressure under the zero osmotic pressure difference condition according to the present invention may further comprise a step of transferring a portion (e.g., 1-99%) of the further concentrated solute-containing aqueous solution to the draw chamber to maintain the osmotic pressure of the draw chamber equal to that of the feed chamber, transferring it to a reverse osmosis separator, and then discharging water of the aqueous solution to the outside, and transferring the concentrated aqueous solution to the zero osmotic pressure difference concentrator.

In the present invention, the aqueous solution containing the solute to be concentrated may be one or more selected from the group consisting of seawater, brackish water, volatile fatty acid salts as fermentation products, and small molecular compounds having properties similar to those of the volatile fatty acid salts.

In the present invention, the solution that is introduced into the draw chamber to form the zero/low osmotic pressure difference between the feed chamber and the draw chamber may be selected from the group consisting of: (1) a portion of the concentrated aqueous solution transferred to the feed chamber; (2) a solution obtained by adding a liquid or a solid, which increases the osmotic pressure and is easily separable, to the aqueous solution of (1); and (3) a solution prepared so as to contain the same components as those of the feed solution and have the same osmotic pressure as that of the feed solution.

In the present invention, the ratio of the volume of the feed chamber to the draw chamber of the zero osmotic pressure difference concentrator may be 100 to 1:1.

In the present invention, concentration by the zero osmotic pressure difference concentrator is performed in a batch manner or a continuous manner in order to maximize the effect thereof.

In the present invention, the feed chamber and the draw chamber are composed of multiple stages.

In the present invention, the aqueous solution may have a pH of 3-11 and a temperature at which water is maintained in liquid state.

In the present invention, a process of independently recovering each of the solute and water from the aqueous solution further concentrated in the zero osmotic pressure difference concentrator may be selected from the group consisting of a multi-stage flash process, a distillation process, a pervaporation process, a thermal decomposition process, a sulfuric acid process, and an ammonia, sodium or calcium salt precipitation process.

Other features and embodiments of the present invention will be more apparent from the following detailed descriptions and the appended claims.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

It is already well known that energy required for reverse osmosis processes is much lower than that of conventional multi-stage flash processes that use heat. In addition, in the case of forward osmosis processes that recently started to be studied, energy larger than expected is required, and a draw solution is lost. Thus, it is known that the forward osmosis process is not highly useful for seawater desalination compared to the reverse osmosis process.

Unlike the case of seawater desalination, when an aqueous solution containing high-value-added small molecular compounds is concentrated by reverse osmosis, it can be economically efficient. However, equipment and energy costs act as burdens, because a thermal process such as a multi-stage flash (MSF) process should be used to regenerate the draw solution.

In addition, a fermentation product can be easily concentrated four times (from 3.5% to 14% (on a solvent basis) by forward osmosis. However, the fermentation product concentration required in the fermentation industry broadly ranges from 20-60 wt % of a saturated aqueous solution of a salt to a 99.5% ethanol purity, and a desired object is difficult to achieve by forward osmosis alone.

In addition, forward osmosis processes have shortcomings in that, because a high concentration of a draw solution is used, it can be diffused to a feed chamber and mixed with a feed solution, and if the solute rejection rate of the feed solution is 100% or lower, it will be difficult to recover the solute from the draw solution.

The present inventors have found that, when water of an aqueous solution containing a variety of solutes to be concentrated is discharged to the outside using a reverse osmosis separator, and the concentrated aqueous solution is introduced into the feed chamber of a concentrator comprising the feed chamber and a draw chamber, which are separated from each other by a reverse osmosis membrane or a forward osmosis membrane, after which a solution having an osmotic pressure equal to or slightly higher than that of the aqueous solution introduced into the feed chamber is introduced into the draw chamber, the osmotic pressure difference ($\Delta\pi$) between the feed chamber and the draw chamber will approach zero ($\Delta\pi=0$), and thus the feed solution can be concentrated even at low pressure.

Figure 1:
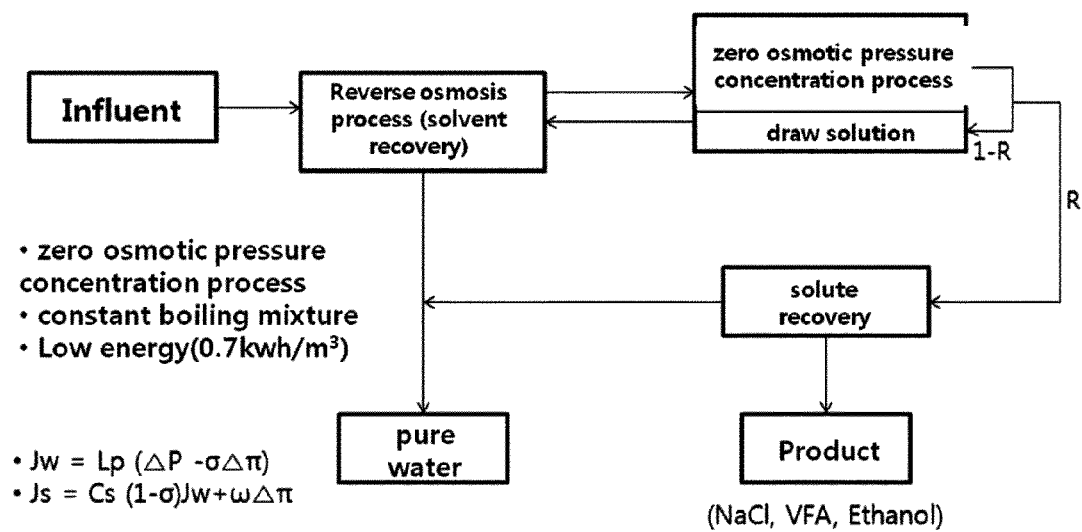
FIG. 1 is a conceptual view showing a method of concentrating an aqueous solution by hydraulic pressure under a zero/low osmotic pressure difference condition according to the present invention.

FIG. 1 is a conceptual view showing a method of concentrating an aqueous solution by hydraulic pressure under a zero/low osmotic pressure difference condition according to the present invention.

As shown in FIG. 1, the concept of feed solution concentration under a zero/low osmotic pressure difference condition comprises a process of regenerating pure water by reverse osmosis and a process of concentrating a feed solution under a zero/low osmotic pressure difference, and the solution concentrated in the zero/low osmotic pressure concentration process can be subjected to a final water removal process to remove water, thereby recovering the solute. At this time, a small amount of the water is also recovered, and thus the water and solute contained in the solution are all recovered.

"R" in FIG. 1 is a measure indicating the degree of recovery of the concentrated solution from the concentration process. Specifically, R=0 means that the concentrated solution is not at all recovered, and R=1 means that the concentrated solution is completely recovered.

In the forward osmosis process, a draw solution should be externally supplied to maintain the osmotic pressure of the draw chamber in order to recover all of the concentrated solution, and for this reason, an additional process of regenerating the diluted draw solution was required.

Thus, in the present invention, 90% of the concentrated solution may be recovered (R=0.9), and 10% of the concentrated solution may be used to maintain a zero/low osmotic pressure difference between the feed chamber and the draw chamber.

In an example of the present invention, it was found that, when hydraulic pressure was applied under a zero/low osmotic pressure difference, seawater, VFA-Na or the like could be concentrated using a relatively low hydraulic pressure until the concentration of the solute reached 100%, and in the case of high-concentration ethanol (e.g., 94% or higher), there was a shortcoming in that a large amount of the concentrated solution would be transferred to the draw chamber in order to reduce the external hydraulic pressure. One big advantage is that, even when the solute moves from the feed chamber to the draw chamber, an additional separation process is not required, and that the rejection rate of the membrane does not need to be so high. The technology of the present invention can be applied to the concentration of not only VFA-salt and NaCl, but also solutions having high osmotic pressure, such as ethanol.

Figure 2:
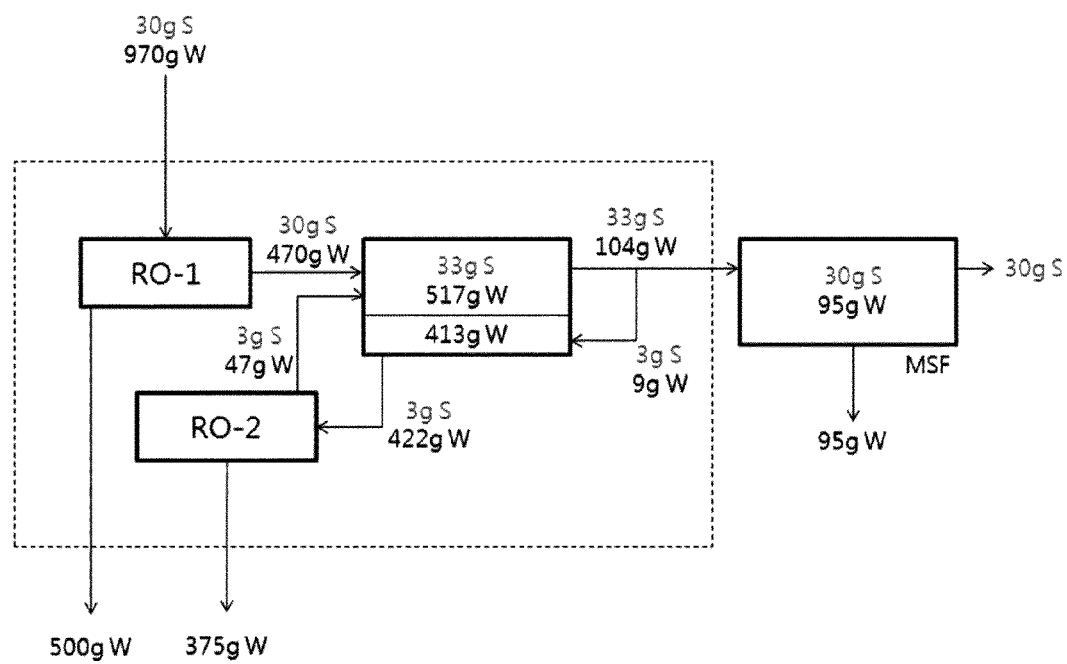
FIG. 2 schematically shows a mass balance in a method of concentrating an aqueous NaCl solution by hydraulic pressure under a zero/low osmotic pressure difference condition according to an embodiment of the present invention.

FIG. 2 schematically shows a mass balance in a method of concentrating an aqueous NaCl solution at low pressure under a zero/low osmotic pressure difference condition according to an embodiment of the present invention.

In FIG. 2, influent consists of 970 g of water and 30 g of salt, and 970 g of water and 30 g of salt are discharged from the section defined by the dotted line. Thus, the total amount of the solute and solvent of the influent is equal to that of effluent.

In the case of the water, 500 g is recovered from RO-1 (reverse osmosis separator), 375 g is recovered from RO-2 (reverse osmosis separator), and 95 g is recovered from the final solid recovery unit (e.g., MSF). Thus, a total of 970 g of water is completely recovered. In addition, 30 g of salt is also completely recovered from the solid recovery unit.

The final concentrated water concentrated in the zero osmotic pressure difference concentrator consists of 33 g of NaCl and 104 g of water, and corresponds to 24%. 90.9% of the final concentrated water is recovered, and 9.1% is recycled so that the draw chamber will have the same osmotic pressure as that of the feed chamber. Specifically, the final concentrated water is diluted in the feed chamber water that permeated from the draw chamber by reverse osmosis, and 3 g of salt and 422 g of water are transferred to RO-2 (reverse osmosis separator) in which 375 g is then regenerated and concentrated. Then, the concentrated water is combined with the influent to RO-1 (reverse osmosis separate) and introduced again into the zero osmotic pressure difference concentrator.

The solute concentration of the influent to the zero osmotic pressure difference concentrator is 6%, and the solute concentration of the effluent is 24%, indicating that the influent is concentrated four times. The calculated osmotic pressure of the saturated concentrated water is 120 bar for NaCl, 100 bar for VFA-Na, and about 1865 bar for 95 wt % ethanol. However, because there is no osmotic pressure difference, a pressure of 50 bar can be used in conventional RO processes, and in the case of ethanol, an operation is possible even at low pressure. Thus, the present invention does not require high pressure.

For reference, energy consumption in a seawater desalination process employing reverse osmosis can be estimated as follows. Pressure (P) applied to reverse osmosis can be expressed $\Delta P+Ps$, wherein $\Delta P$ is an overpressure for resisting membrane resistance, and Ps is osmotic pressure (Optimizing the Efficiency of Reverse Osmosis Seawater Desalination, http://urila.tripod.com/Seawater.htm). Thus, required minimum work (W) is P×V. Thus, at Ps=27 bar, the minimum work (W) required to produce 1 ton of water is 27.1/36=0.75 kwh.

Referring to FIG. 2 again, 500 g of water can be recovered from RO-1, and 375 g of water can be recovered from RO-2, indicating that a total of 875 g of water can be recovered. The amounts of energy required in the reverse osmosis separator, the zero osmotic pressure difference concentrator and the final solid recovery unit are as follows:

(1) RO-1 and RO-2: $0.875 \text{ kg/m}^3 \times 0.75 \text{ kwh} = 0.656 \text{ kwh} + 0.875 \text{ kg} \times \Delta P$;

(2) zero osmotic pressure difference concentrator (unit): $0.413 \text{ kg} \times \Delta P$;

(3) final solid recovery unit (e.g., MSF): $0.095 \text{ kg} \times \Delta P$.

Energy consumption by $\Delta P$ is $0.875+0.413+0.095=1.383 \times \Delta P$. This energy can be irreversibly used so as to change into heat, but can also be recovered by an energy recovery unit. Given the amounts of energy are 0 kwh, 0.25 kwh, 0.5 kwh and 0.75 kwh, then 0.656 kwh, 1.001 kwh (=0.656+1.383×0.25), 1.346 kwh (=0.656+1.383×0.5), 1.691 kwh (=0.656+1.383×0.75) are obtained.

When a conventional reverse osmosis process is used, the recovery of water is only 50-60%. However, when an aqueous solution is concentrated at low pressure under a zero osmotic pressure condition, there are advantages in that almost 100% of water is recovered, and the solute is completely recovered, indicating that the concentration process is highly value added.

In order to concentrate an aqueous solution at low pressure under a zero osmotic pressure condition, the osmotic pressure of the feed solution should be previously understood. Specifically, the osmotic pressure of solution to be measured can be determined by placing a solution whose osmotic pressure is known in one chamber of a forward osmosis reactor, placing the solution to be measured in the other chamber, and then measuring the direction of movement of the water.

Figure 5A:
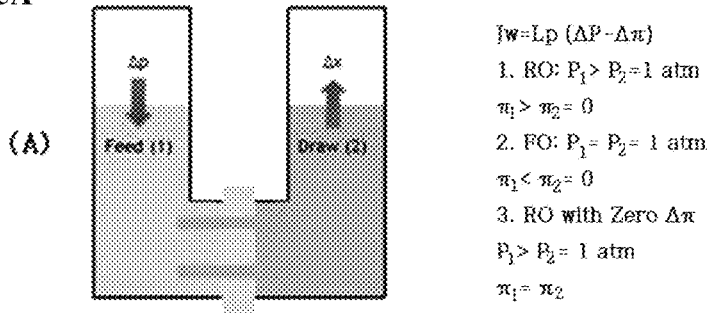
FIG. 5A illustrates a device for comparing the osmotic pressure in a solute solution to determine static equilibrium according to an embodiment of the present invention ((a): a view illustrating static equilibrium achieved by osmotic pressure in a feed chamber and a draw chamber; and (b): photographs showing static equilibrium achieved by osmotic pressure)
Figure 5A:
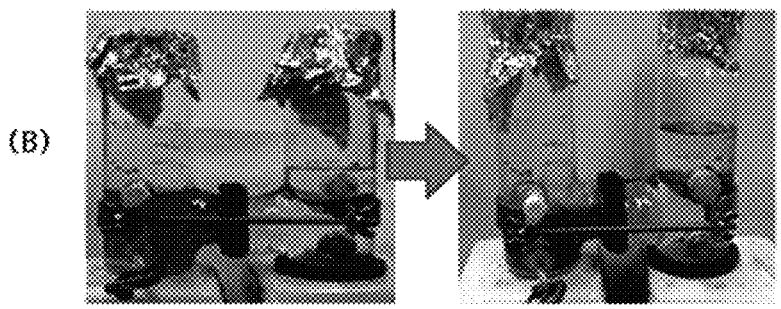

For example, as shown in FIG. 5A, when a VFA solution having a VFA concentration of 3.5 wt %, prepared by mixing acetic acid, propionic acid and butyric acid, is placed in a feed chamber and 5M NaCl (estimated value: 108 bar; see Lenntech) having high osmotic pressure is placed in a draw chamber, it can be seen that the solutions reach equilibrium after 48 hours. At this time, the VFA concentration of the VFA solution in the feed chamber was 14% based on the solvent, and thus the concentration increased 4 times, suggesting that 75% of the water moved from the left side 1 to the right side 2. As calculated using equation (4), the theoretical osmotic pressure of the 3.5% VFA aqueous solution is 10 atm, and the theoretical osmotic pressure of the 14% VFA aqueous solution is 40 atm, and as calculated using equation (3), the theoretical osmotic pressure of the 3.5 wt % VFA solution (adjusted to pH 8 with an NaOH solution) is about 8 atm ((Lenntech (http://www.lenntech-.com/calculators/activity/activity-coefficient.htm), accessed on Jan. 20, 2014).

As described above, when the same or different materials are placed in the feed chamber and the draw chamber and the movement of the water is observed, a chamber having higher osmotic pressure among the two chambers can be easily seen.

However, because of concentration polarization due to incomplete mixing between the two chambers, it is difficult to determine accurate flux.

Figure 5B:
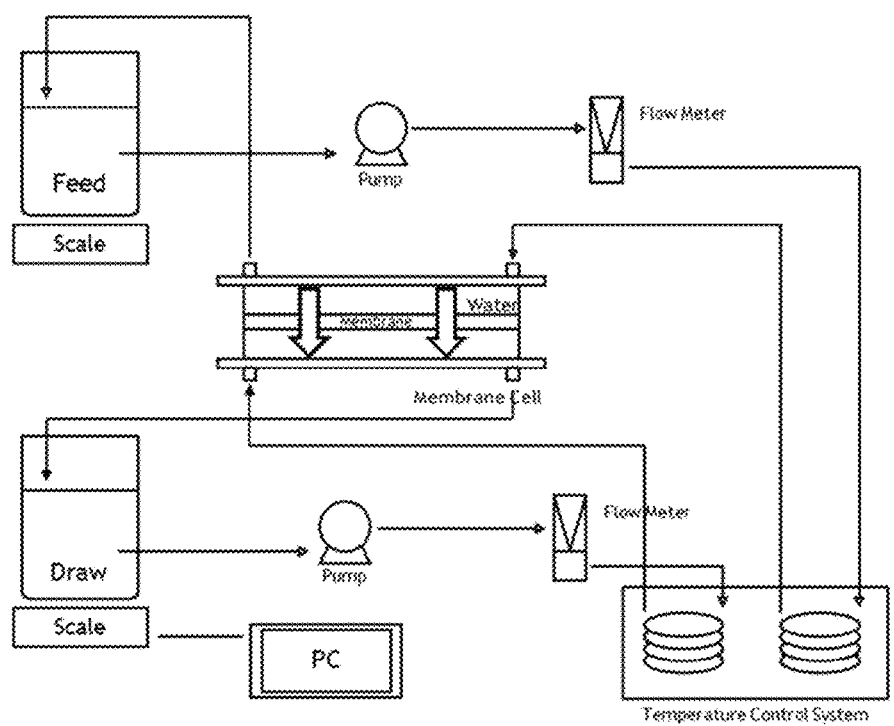
FIG. 5B illustrates a system of measuring the flux of a membrane in a high-concentration solute solution using a lab-scale flow-recirculation set according to an embodiment of the present invention.

Thus, as shown in FIG. 5B, it is preferable to measure the flux of the membrane in a high-concentration solute solution using a flow recirculation set.

The flow recirculation set is provided with a scale so that it can measure the weight of each of the feed chamber and the draw chamber. Thus, it can measure flow movement between the chambers in real time and can measure the flux of the membrane by the change in concentration between the chambers.

In addition, when the flow recirculation set is used, the initial concentration and final concentration in the feed chamber can be measured, thereby obtaining the time required for concentration, data (membrane area, etc.) required for scale up, etc. Based on such data, the size of a membrane system, the degree of separation, etc., can be estimated, and particularly, the sizes of the feed chamber and the draw chamber can be determined.

In one aspect, the present invention is directed to a method of concentrating an aqueous solution containing a solute to be concentrated, at low pressure under a zero osmotic pressure difference condition, the method comprising the steps of: (a) firstly concentrating the solute-containing aqueous solution to be concentrated by reverse osmosis; (b) introducing the firstly concentrated solute-containing aqueous solution of step (a) into a zero osmotic pressure difference concentrator comprising a feed chamber and a draw chamber, which are separated from each other by a reverse osmosis membrane or a forward osmosis membrane, thereby secondly concentrating the introduced solute-containing aqueous solution in the concentrator; and (c) recovering the secondly concentrated solute-containing aqueous solution while recycling a portion of the secondly concentrated solute-containing aqueous solution to the draw chamber to form a zero osmotic pressure difference between the feed chamber and the draw chamber.

In the present invention, step (b) comprises the steps of: (i) transferring the firstly concentrated aqueous solution of step (a) to the feed chamber of the zero osmotic pressure difference concentrator, and introducing into the draw chamber either a solution having an osmotic pressure identical to that of the aqueous solution transferred to the feed chamber, thereby forming the zero osmotic pressure difference between the feed chamber and the draw chamber; and (ii) applying a pressure of 0-5 atm for the forward osmosis (FO) membrane or 10-200 atm for the reverse osmosis membrane to the feed chamber under the zero osmotic pressure difference condition to transfer water of the concentrated aqueous solution to the draw chamber, thereby further concentrating the concentrated aqueous solution.

If pressure that is applied to the feed chamber is too high, the membrane can be broken in forward osmosis (FO) to lose its function. In the case of reverse osmosis, it can be difficult to manufacture a membrane or a membrane module, which can resist a pressure of up to 250 atm which is used by current high-pressure pumps.

The method of concentrating the aqueous solution at low pressure under the zero osmotic pressure difference condition according to the present invention may further comprise a step of transferring a portion (e.g., 1-99%) of the further concentrated solute-containing aqueous solution, preferably an estimated value (e.g., 10%) calculated from the mass balance and pressure balance described in the example, to the draw chamber to maintain the osmotic pressure of the draw chamber equal to that of the feed chamber, transferring it to a reverse osmosis separator, and then discharging water of the aqueous solution to the outside, and transferring the concentrated aqueous solution to the zero osmotic pressure difference concentrator.

In the present invention, an aqueous solution that is introduced into the draw chamber in order to maintain the zero osmotic pressure condition may be selected from the group consisting of the aqueous solution transferred to the feed chamber, methanol, ethanol, an ammonium carbamate-containing solution, a highly osmotic waste solution, a calcium chloride-containing solution, and a magnesium chloride-containing solution.

Herein, the aqueous solution in the draw chamber may be transferred to either the reverse osmosis separator (RO-1) used before the zero osmotic pressure concentration process, or another reverse osmosis separator (RO-2).

In the present invention, in order to maintain the zero osmotic pressure difference between the draw chamber and the feed chamber, it is preferable that the volume of the draw chamber be smaller than that of the feed chamber and the retention time of the aqueous solution in the chamber be short.

Specifically, given the recovery of the concentrated water is 90%, the volume ratio of the draw chamber to the feed chamber of the zero osmotic pressure difference concentrator is preferably 1/10 in order to maintain the retention time equal to that in the feed chamber, and is preferably 1/100 in order to maintain the retention time shorter, and is preferably 1/1 in order to maintain the retention time longer.

The zero osmotic pressure difference concentrator according to the present invention may be composed of a plurality of stages. Namely, the feed chamber and draw chamber of the zero osmotic pressure difference concentrator may be composed of a plurality of stages.

Figure 3:
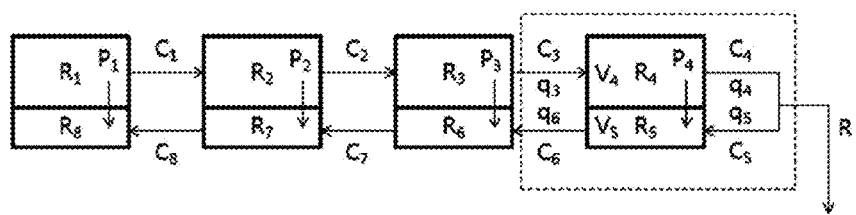
FIG. 3 schematically shows a method of maintaining a zero osmotic pressure difference in the draw chamber of a zero osmotic pressure difference concentrator according to the present invention.

FIG. 3 schematically shows a method of maintaining the osmotic pressure in the draw chamber of a zero osmotic pressure difference concentrator according to the present invention.

If the aqueous solution concentrated using the zero osmotic pressure difference concentrator is not recovered, the concentration will be meaningless. However, in the present invention, about 90 wt % of the aqueous solution concentrated in the zero osmotic pressure difference concentrator is recovered, and 10 wt % is transferred back to the draw chamber in order to maintain the osmotic pressure of the draw chamber equal to the osmotic pressure of the feed chamber.

In FIGS. 3, V4 and V5 in the area defined by the dotted line mean the volume of the feed chamber and the volume of the draw chamber, respectively, and P4 means the total amount of the permeated water obtained under the zero osmotic pressure condition.

C4 that is the concentration of the concentrated water increases as P4 increases, compared to C3 that is the concentration of the water concentrated in the zero osmotic pressure difference concentrator. Also, C4 increases with an increase in q4 that is the flow rate of influent to the fourth chamber. C4 and C5 are the same, but when 90% of q5 that is the flow rate of influent to the fifth chamber is recovered, it can be 1/10 of q4.

In order to maintain the zero osmotic pressure difference, the retention time in the feed chamber and the draw chamber can be controlled. Specifically, when the recovery of the concentrated water is 90%, (1) V5 can be about 1/10 of V4 in order to maintain the retention time in the feed chamber equal to that in the draw chamber; (2) V5/V4 can be 1/100 of v4 in order to make the retention time in the draw chamber shorter than that in the feed chamber; and (3) V5/V4 can be controlled in order to make the retention time in the draw chamber longer than that in the feed chamber. In the case of (1), given the retention time in each of V4 and V5 is 10 hours and the amount of solution (or water) passing through the membrane is P4, q5 is then q5+P4. At this time, C5 is q5/(q5+P4)C5. In the case of (2), given the retention time is 1/10, C5 is q5/(q5+1/10P4)C5. This is because P4 is influenced by the retention time. In the case of (3), given the retention time is 10 times, C5 is q5/(q5+10P4)C5. In other words, given the influence in the case of (1) is about 1/10, the influence in the case of (2) is 1/10 of (1), and P4 in the case of (3) is 10 times larger. Of course, although water can be added to the draw chamber to provide the effect of diluting the concentration, the reverse osmosis state can be maintained by external pressure ΔP. The method of increasing the recovery (R) of the product from the zero osmotic pressure system is (2). In the case of (2), the retention time in the draw chamber can be made as short as possible unless there is no problem in the terms of design/operation, whereby the concentration of the draw solution can be maintained as high as possible, thereby ensuring the zero osmotic pressure difference between the chambers. Details will be described in the examples of the present invention.

Generally, the amount of the permeated water (P4) that passed through the membrane is smaller than q5 that is the flow rate of influent to the forth draw chamber and q5 that is the flow rate of influent to the forth feed chamber. In other words, the osmotic pressure of the draw chamber can be maintained equal to or lower than the osmotic pressure of the feed chamber.

In another method for maintaining the osmotic pressure in the draw chamber of the zero osmotic pressure difference concentrator according to the present invention, an osmolyte having a high effect of inducing osmotic pressure may be introduced into a portion of the draw chamber, but there is a problem in that regeneration is required.

In the present invention, as a reverse osmosis membrane or forward osmosis membrane that separates the feed chamber from the draw chamber, any membrane may be used without particular limitation, as long as it mainly passes a solvent without passing a solute therethrough.

As used herein, the term "solute" refers to a liquid or solid material that dissolves in water as a solvent.

In the present invention, "aqueous solution containing solutes to be concentrated" includes seawater, brackish water, cellular metabolites, reaction products, etc. Herein, the cellular metabolites are intended to include animal cells, plant cells, microorganisms, microbial primary metabolites, microbial secondary metabolites, secreted microbial proteins, biotransformations, etc.

Examples of the reaction solutions include chemical reaction products and enzymatic reaction products.

Examples of the microbial primary products include, but are not limited to, volatile fatty acids (acetic acid, propionic acid, butyric acid, lactic acid, citric acid, succinic acid, etc.), alcohols (ethanol, butanol, etc.), nucleic acids, amino acids (lysine, tryptophan, etc.), vitamins, polysaccharides and the like.

Examples of the microbial secondary metabolites include, but are not limited to, antibiotics (penicillin, etc.), enzyme inhibitors, physiologically active substances (Taxol, etc.).

Examples of the excreted microbial proteins include, but not limited to, enzymes such as amylase and cellulose, insulin, interferon, monoclonal antibodies, etc. The biotransformations are substances produced using microorganisms or enzymes and may be exemplified by, but not limited to, steroids.

Figure 4:
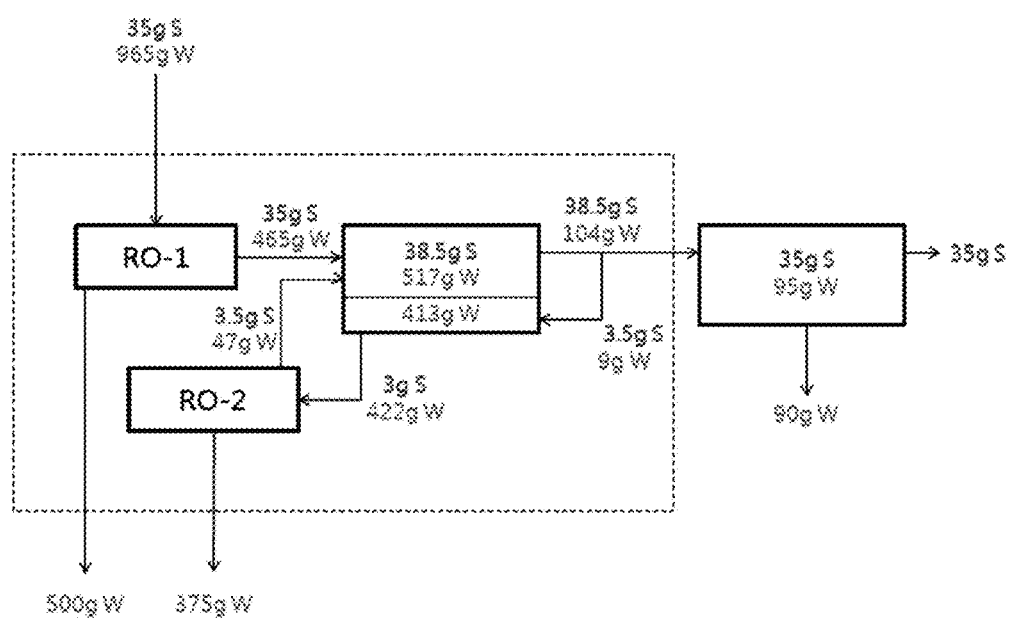
FIG. 4 schematically shows a mass balance in a method of concentrating an aqueous solution of mixed organic acids by hydraulic pressure under a zero/low osmotic pressure difference condition according to an embodiment of the present invention.

For example, in the case in which ethanol is concentrated using a system comprising the reverse osmosis separator and the zero osmotic pressure difference concentrator as shown in FIG. 2 or 4, the concentration of ethanol that can be concentrated in the reverse osmosis concentrator (RO-1) is 20%. Theoretically, it is known that ethanol can be concentrated to 20-100% by the zero osmotic pressure process. However, a membrane capable of concentrating ethanol to 91-100%, like volatile fatty acids (VFA), has not yet been developed.

Because volatile fatty acid (VFA) has a degree of saturation of about 50-60 wt %, it can be theoretically concentrated to 100%. In addition, it has a high rejection rate, and thus can be concentrated to 100% even under a zero osmotic pressure difference condition.

In the present invention, the solution may have a pH of pH of 2-13 and a temperature at which water is maintained in liquid state, for example, 0-100° C., preferably 15-50° C., more preferably 20-40° C. The temperature may be higher or lower than the above temperature. For example, a mixture of other solute/solvent may have a temperature deviating from the above temperature.

In the present invention, the solution that is introduced into the draw chamber in order to form a zero osmotic pressure difference condition between the feed chamber and the draw chamber may be a concentrated aqueous solution transferred to the feed chamber, a solution that is easily separated after use, etc. However, the solution is preferably an aqueous solution having the same composition as that of the concentrated aqueous solution transferred to the feed chamber.

In the present invention, concentration by the zero osmotic pressure difference concentrator may be performed in a batch manner or a continuous manner in order to maximize the effect thereof.

The batch manner may be performed when the two chambers do not communicate with an external system, and the continuous manner may be performed when the two chambers communicate with an external system.

In the present invention, the feed chamber and the draw chamber may be composed of multiple stages.

In the present invention, recovery of the solute and water from the aqueous solution concentrated in the zero osmotic pressure difference concentrator can be performed using a multi-stage flash process, a pervaporation process, a thermal decomposition process, a sulfuric acid process, a calcium process, etc., but is not limited thereto. The step of recovering water from the concentrated aqueous solution may be performed during step (a) of concentrating an aqueous solution containing a solute to be concentrated, using reverse osmosis; or step (b) of introducing the concentrated solute-containing aqueous solution into a zero osmotic pressure difference concentrator comprising a feed chamber and a draw chamber, which are separated from each other by a membrane, and further concentrating the introduced concentrated aqueous solution; or (c) recovering the further concentrated solute-containing aqueous solution while recycling a portion of the further concentrated solute-containing aqueous solution to the draw chamber. In addition, the step of recovering the solute may be performed during step (c) of recovering the further concentrated solute-containing aqueous solution while recycling a portion of the further concentrated solute-containing aqueous solution to the draw chamber.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Figure 6A:
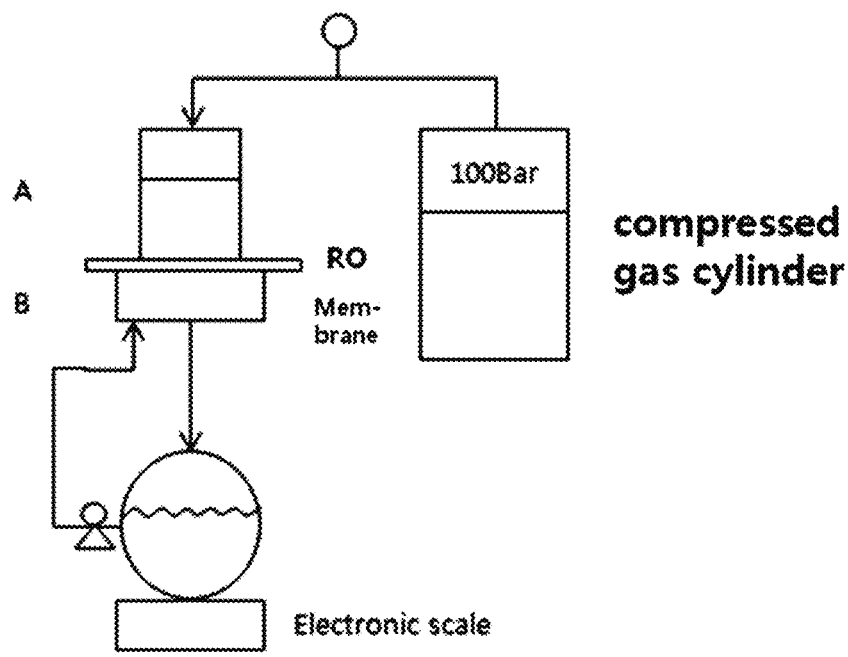
FIG. 6A illustrates a zero-osmotic-pressure batch system comprising a high-pressure feed chamber (a) and an atmospheric-pressure draw chamber (b)
Figure 6B:
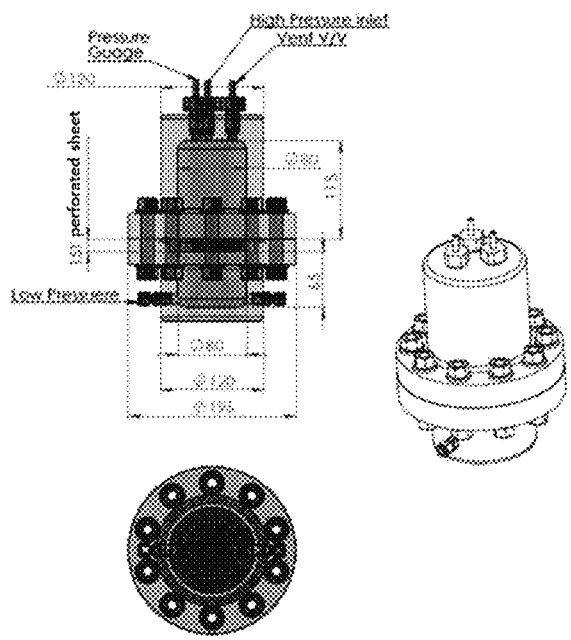
FIG. 6B shows the details of (a) and (b) of FIG. 6A.

Example 1: Concentration of NaCl Aqueous Solution Using Zero Osmotic Pressure Difference Concentrator In the system as shown in FIG. 6A, a sample (NaCl aqueous solution) was placed, and pressure was applied thereto. The amount (weight) of sample that passed from high-pressure chamber A to chamber B (atmospheric pressure) through an RO membrane for a given time was measured.

The membrane used in this Example was RE2521-TL (Woongjin Chemical Co., Ltd., Seoul, Korea; http://www-.csmfilter.com), which is a thin-film composite type RO membrane which is used in a negatively charged, polyamide, spiral-wound module. The membrane has a permeability of 1.1 m$^3$/day and an effective area of 1.1 m$^2$. It rejects 99% of 1,500 mg/L at 1.0 MPa, and shows a maximum pressure of 4.14 MPa, a maximum flow rate of 1.36 m$^3$/hr, and a minimum flow rate (concentrate) of 0.23 m$^3$/hr. It has a maximum temperature of 45° C. and a pH of 3.0-10.0, and can also resist a pH of 2.0-11.0.

500 ml of an NaCl solution having the composition shown in Table 2 below was placed in each of chambers A and B, and the amount of solution moved with the passage of time appeared as the weight of chamber B. Thus, this amount was monitored by a computer. For NaCl, a conductivity meter (CM-31p, TOADKK, Japan) was used, and for VFA-Na, HPLC (YoungLin, Korea) was used.

In Table 2 below, the amount of a saturated solution of NaCl is 359 g per 1000 g of water, and thus 80% of the amount of a saturated solution of NaCl is 22.3 wt %, and 60% is 17.7%.

22.3 wt % is 4.9 M (mole, based on 1000 g of water), and 17.7 wt % is 3.68 M. The estimated osmotic pressures in the feed chamber and the draw chamber are 97 bar and 68 bar, respectively. As can be seen in Table 1 above, the same material was introduced into the feed and draw chamber at the same concentration to make a zero osmotic pressure difference condition (22.3%, and 22.3%), and then an experiment was performed. As a result, w-flux was 0.6634, and 17.7% and 22.3% were higher in the draw chamber, indicating that it was an forward osmosis environment. In this case, the flux was 0.8798, indicating that flux was present in the zero osmotic pressure difference environment at ΔP (30 bar).

In the zero osmotic pressure difference environment of 17.7% and 17.7% (ΔP=5-30 bar), it can be seen that water is easily permeated, and an increase in ΔP leads to an increase in w-flux (from 0.2994 to 0.7475). In this experiment, a linear relationship of w-flux(L/m$^2$·h)=0.025ΔP can be seen, wherein 0.025 is expressed in units of L/(m$^2$·h·bar). In addition, at the same pressure (30 bar) and a higher concentration (22.3-22.3), w-flux is 0.6634, whereas it is 0.7475 at a concentration of 17.7-17.6, indicating that w-flux is higher at lower concentrations.

Example 2: Concentration of VFA-Na Aqueous Solution Using Zero Osmotic Pressure Difference Concentrator Using the membrane and test system used in Example 1 (concentration of NaCl), an experiment was performed using volatile fatty acid-Na as a sample under the following zero osmotic pressure difference conditions.

TABLE 2

Concentration of NaCl under zero osmotic pressure condition

NaCl (Feed Concentration - Draw Concentration), 22.3 wt %~22.3 wt %; 17.7 wt %~22.3 wt %; 17.7%~17.7; $F_c$: Concentration in feed after experiment

| Operation Condition | Pressure (bar) | $F_m$—NaCl (g) | Water Permeation (ml) | Residual Solution (ml) | $F_c$—NaCl (g/L) | w-flux | rejection (%) |
|---|---|---|---|---|---|---|---|
| 22.3-22.3 | 30 | 143.6 | 13.34 | 486.66 | 295.0 | 0.6634 | 100 |
| 17.7-22.3 |    | 107.7 | 17.69 | 482.31 | 223.3 | 0.8798 | 100 |
| 17.7-17.7 | 5  | 107.7 | 6.02  | 493.98 | 218.0 | 0.2994 | 100 |
|           | 10 | 107.7 | 8.41  | 491.59 | 219.0 | 0.4182 | 100 |
|           | 20 | 107.7 | 10.14 | 489.86 | 219.8 | 0.5043 | 100 |
|           | 30 | 107.7 | 15.03 | 484.97 | 222.07 | 0.7475 | 100 |

All the units are given in grams, and $F_m$—NaCl is the total amount of NaCl in the feed chamber.
Concentration was started with 500 g in each of the feed chamber and the draw chamber.
Amount (ml) of water permeated = 500 (ml)-amount (ml) of residual solution.
NaCl remains in the feed chamber with a rejection rate of 100%, and thus is concentrated to an amount corresponding to the amount of permeated water.
w-flux = amount of water permeated/area · time (g/(m$^2$ · h)).
Fc = 143.5/0.48666 = 295.07 (g/L).

TABLE 3

Concentration of VFA-Na under zero osmotic pressure difference conditions

| Operation Condition | Pressure (bar) | F-VFA | Water Permeation (ml) | Residual Solution (ml) | Concentration of D-VFA | w-Flux | rejection (%) |
|---|---|---|---|---|---|---|---|
| 22.77-22.77 | 5 | 147.4 | 2.17 | 497.83 | 296.18 | 0.1079 | 100 |
| | 10 | 147.4 | 2.98 | 497.02 | 296.66 | 0.1482 | 100 |
| | 20 | 147.4 | 3.95 | 496.05 | 297.24 | 0.1964 | 100 |
| | 30 | 147.4 | 4.11 | 495.89 | 297.34 | 0.2044 | 100 |

VFA (Feed concentration - Draw concentration), 22.77 wt %~22.77%

All the units are given in grams, w-flux = amount of water permeated/area · time (g/(m$^2$ · h)).

As can be seen in Table 3 above, 1000 g of water contains 294.8 g (22.77 wt %) of VFA-Na. The molar concentration of VFA-Na is 3.73 M. The osmotic pressure is 67 bar. At the same molar concentration, 17.7 wt (3.68 M) of NaCl shows a w-flux of 0.7475 at 30 bar, whereas VFA-Na shows a w-flux of 0.2044, which is significantly lower.

Example 3: Concentration Process (FO) Under Zero Osmotic Pressure Difference Condition Using pressure-assisted osmosis, an experiment on the concentration of NaCl solution was performed. The membrane used in the forward osmosis process was a cartridge (Hydration Technologies, USA) made of cellulose triacetate.

In a conventional forward osmosis process, a solute having high osmotic pressure is used in a draw chamber, but in this Example, the same solute as that used in the feed chamber was used in the draw chamber. The following experiment can be an experiment on the application of a zero osmotic pressure difference to forward osmosis.

Specifically, as a feed solution, NaCl solutions corresponding to 80% (287 g/L) and 60% (215 g/L) of the solubility of NaCl (359 g/L) were used, as a draw solution, 100% (359 g/L) NaCl aqueous solution was used. The draw solution was used in the experiment after it was adjusted to pH 8 using ammonia water, and an external pressure of 20 psi (1.36 atm, 1.38 bar) was applied.

Concentration was performed using 1 liter of each of the feed solution and the draw solution, and the results are shown in Table 4 below.

TABLE 4

Concentration by application of 1.3 atm in forward osmosis process

| Experiment | Solution | Start Concentration (wt %) | Final Concentration (wt %) |
|---|---|---|---|
| I Water Movement (92.32 g) | Feed Solution | 287 g-NaCl/Water 1000 g (22.3) | 287 g-NaCl/w- 907.68 g (24.02) |
| | Draw solution | 359 g-NaCl/water 1000 g (26.4) | 359 g-NaCl/w- 1122.68 g (24.23) |
| II Water Movement (213.4 g) | Feed solution | 215 g-NaCl/water 1000 g (17.6) | 215 g-NaCl/w- 786.6 g (21.46) |
| | Draw solution | 359 g-NaCl/water 1000 g (26.4) | 359 g-NaCl/w- 1213.4 g (22.83) |

As can be seen in FIG. 4, when the high-concentration NaCl solution was used as both the feed solution and the draw solution in the lab-scale pressure-assisted forward osmosis process and external pressure is applied, the water could move from the feed chamber to the draw chamber to increase the concentration of NaCl. In experiment 1, the draw solution was diluted from 26.4 wt % to 24.23 wt %, and the feed solution was concentrated from 22.3 wt % to 24.02 wt %. In experiment 2, the feed solution was concentrated from 17.6 wt % to 21.46 wt %, and the draw solution was diluted from 26.4 wt % to 22.83 wt %.

Example 4: Continuous Concentration Process Under Zero Osmotic Pressure Difference Condition The concentrations of solutions in feed chamber (R4) and draw chamber (R5), which are the last chambers in the zero osmotic pressure process and are defined by the dotted line in FIG. 3, need to be compared to each other. If the concentrations of the two solutions are the same, it can be said that there is no osmotic pressure difference between the two chambers. Because it is a continuous stirred tank reactor/separator (CSTR), the concentration in the feed chamber is C4, and the concentration in the draw chamber is C6. That is, the concentrations of C4 and C6 are compared to each other to determine whether external pressure can be equal to the difference between the osmotic pressures π4 and π6 corresponding to the concentrations C4 and C6.

As can be seen in FIG. 3, regarding the difference between C4 and C6, C4 minus C6 is [C3(1+P4/q4)/(1+P4/q5)]*[1−1/(1+P4/q5)]≅C3*P4/q5, because P4/q4 and P4/q5 are <<1. Of cause, q5 is ≤q4, because q5 uses a portion of q4. If the recovery (R) is 0, q5 is equal to q4, and if R is 1, q5 is equal to 0. In summary, C4 minus C6 is equal to PQ*C3, wherein PQ is the ratio of P4-permeate to draw flow rate-q5 and is P4/q5)*C3. The osmotic pressure difference between C4 and C6 is expressed as PQ*C3, and if externally applied pressure ΔP is higher than the osmotic pressure difference (C4-C6), a process under a zero osmotic pressure difference is possible. This PQ can be controlled by recovery (R) such that P4/q5 is smaller than 1, or a higher ΔP value can be used. In addition, if the multi-stage separator is operated like a plug flow reactor (PFR), P4 is proportional to the membrane area, but q5 is not so, and thus PQ can be maintained smaller than 1.

For example, at P4=1 m$^3$/m$^2$·d and q4=5.52 m$^3$/m$^2$·d (CSM RE2521-TL catalog in Example 1) and R=0, the solution is completely recycled, PQ44 is 0.18, and at R=0.5, PQ45 is 0.36. However, the above values are high, because these are data provided by the manufacturer and obtained at a very low solute concentration. However, P4 determined by the present inventors at high concentrations is 0.74 L/(m$^2$·h)×24=18 L/(m$^2$·d)=0.018 m3/m$^2$·d, which is the highest value obtained in Examples 1 and 2.

If q5 is 10% of q4=5.52, it is then P4/q5=0.018/0.552=about 0.032. An osmotic pressure of πf−πd=Δπ

(0.032C3)<external pressure ΔP may be applied. NaCl has an osmotic pressure of about 128 bar at a saturated concentration of 6.14 M, and 3% thereof is only 3.84 bar. In subsequent processes (C3-C7 and C2-C8), the osmotic pressure difference can be easily overcome even by low hydraulic pressure, because the flux is higher, even though the osmotic pressure is lower than that of the above-described processes.

In the defined area in FIGS. 3, V4 and V5 mean the volume of the feed chamber and the volume of the draw chamber, and P4 means the total amount of water that permeated without an osmotic pressure difference.

C4 that is the concentration of concentrated water increases as P4 increases, compared to C3 that is the concentration of water concentrated in the zero osmotic pressure difference concentrator, and C4 increases with an increase in q4 that is the flow rate of effluent from the fourth chamber. This is because q3 is the flow rate of influent to the fourth chamber is the sum of membrane-permeated water P4 and q4. Generally, the above feed chambers are configured such that membrane-permeated water is sent to the draw chamber so that the concentration thereof will increase compared to that in the previous chamber. However, the concentration in the draw chamber can decrease gradually due to a dilution effect because membrane-permeated water is introduced from the feed chamber. A method capable of maintaining the concentration is important in the zero osmotic pressure process. In order to maintain this concentration, in the present invention, (1) controlling the retention time in the draw chamber and (2) diluting the draw solution with an external material having high osmotic pressure while maintaining high osmotic pressure are adopted. Herein, a material having a low molecular weight and high osmotic pressure, such as methanol or ethanol, may be used. 94.5% ethanol has an osmotic pressure of 1800 atm. In the method of (1) is preferably used.

C4 and C5 are the same concentration, but if 90% of q4 is recovered (R=0.9), q5 that is the flow rate of the influent to the fifth chamber can be 1/10 of q4.

In order to maintain the zero osmotic pressure difference, the retention time in the feed chamber and the draw chamber can be controlled. Specifically, when the recovery of the concentrated water is 90%, (1) V5 can be about 1/10 of V4 in order to maintain the retention time in the feed chamber equal to that in the draw chamber; (2) V5/V4 can be 1/100 of v4 in order to make the retention time in the draw chamber shorter than that in the feed chamber; and (3) V5/V4 can be controlled in order to make the retention time in the draw chamber longer than that in the feed chamber. In the case of (1), given the retention time in each of V4 and V5 is 10 hours and the amount of solution (or water) passing through the membrane is P4, q5 is then q5+P4. At this time, C5 is q5/(q5+P4)C5. In the case of (2), given the retention time is 1/10, C5 is q5/(q5+1/10P4)C5. This is because P4 is influenced by the retention time. In the case of (3), given the retention time is 10 times, C5 is q5/(q5+10P4)C5. In other words, given the influence in the case of (1) is about 1/10, the influence in the case of (2) is 1/10 of (1), and P4 in the case of (3) is 10 times larger. Of course, although water can be added to the draw chamber to provide the effect of diluting the concentration, the reverse osmosis state can be maintained by external pressure ΔP. The method of increasing the recovery (R) of the product from the zero osmotic pressure system is (2). In the case of (2), the retention time in the draw chamber can be made as short as possible unless there is no problem in the terms of design/operation, whereby the concentration of the draw solution can be maintained as high as possible, thereby ensuring the zero osmotic pressure difference between the chambers.

Example 5: Application of Zero Osmotic Pressure Process (Seawater Desalination)

The maximum saturation concentration in seawater desalination is 6.14 M. The osmotic pressure corresponding to thus saturation concentration is only 112 atm, and thus if seawater desalination is performed using the zero osmotic pressure process, C3 is lower than 0.076 (10 bar). Thus, a small difference in osmotic pressure can be easily overcome by applying low external pressure.

Example 6: Application of Zero Osmotic Pressure Process (Concentration of VFA)

Given the ratio of acetic acid-Na, propionic acid-Na and butyric acid-Na in a mixture of VFA-Na is 6:1:3, the maximum solubility is 500 g of VFA-Na per 1000 g of water. Given the molecular weight of the mixture is 78, the number of moles thereof is 6.41 M. Herein, the osmotic pressure is about 120 atm, which does not greatly differ from that in seawater desalination, the salt can be concentrated to saturation.

Example 7: Determination of Ethanol Recovery for Concentration of Ethanol

Ethanol for fuel is required to have a purity of up to 99.5%, and the osmotic pressure at this purity is as high as 6053.2 bar as calculated using the Lewis equation (equation 4). 99.0% ethanol has an osmotic pressure as high as 5101.3 bar. As calculated in Example 4, C4 minus C6 is C3*P4/q5, given P4/q4 and P4/q6<<1. Given the osmotic pressure at C3 is about 1865 bar (95% ethanol) and hydraulic pressure that can be applied to the membrane is about 100 atm, P4/q5 is 1/18. Thus, given P4 is 0.018 $m^3/(m^2 \cdot d)$, q5 may be 0.018×18=0.324 $m^3/m^2 \cdot d$ or higher. Thus, the ratio of P4/q5 can be reduced by increasing the recovery of ethanol.

INDUSTRIAL APPLICABILITY

As described above, in the method of concentrating an aqueous solution at low pressure under a zero osmotic pressure difference condition according to the present invention, the aqueous solution can be concentrated to the maximum saturation concentration of a solute or a solution concentration of 100% using a reduced amount of energy without having to use an extraction solvent. In addition, there is an advantage in that a separate osmosis draw solution does not need to be used.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method of concentrating an aqueous solution containing a solute to be concentrated, the method comprising the steps of:
   (a) firstly concentrating, by reverse osmosis, the aqueous solution containing a solute to be concentrated, thereby producing a firstly concentrated solute-containing aqueous solution;

(b) introducing the firstly concentrated solute-containing aqueous solution of step (a) into a zero osmotic pressure difference concentrator comprising a feed chamber and a draw chamber, which are separated from each other by a reverse osmosis membrane, thereby secondly concentrating the introduced solute-containing aqueous solution in the concentrator to produce a secondly concentrated solute-containing aqueous solution; and (c) recovering the secondly concentrated solute-containing aqueous solution, while recycling a portion of the secondly concentrated solute-containing aqueous solution to the draw chamber to form a zero osmotic pressure difference between the feed chamber and the draw chamber, wherein step (b) comprises the steps of:

(i) transferring the firstly concentrated aqueous solution of step (a) to the feed chamber of the zero osmotic pressure difference concentrator, and introducing into the draw chamber the aqueous solution transferred to the feed chamber having an osmotic pressure identical to that of the aqueous solution transferred to the feed chamber, thereby forming the zero osmotic pressure difference between the feed chamber and the draw chamber; and (ii) applying a pressure for the reverse osmosis membrane to the feed chamber under the zero osmotic pressure difference condition to transfer water of the concentrated aqueous solution to the draw chamber, thereby further concentrating the concentrated aqueous solution; and wherein step (c) comprises the steps of:

(i) transferring 10 wt %-90 wt % of the secondly concentrated solute-containing aqueous solution to the draw chamber to maintain the osmotic pressure of the draw chamber equal to that of the feed chamber;

(ii) transferring solute-containing aqueous solution from the draw chamber to a reverse osmosis separator to produce a thirdly concentrated solute-containing aqueous solution, and discharging water of the solute-containing aqueous solution to outside; and (iii) transferring the thirdly concentrated solute-containing aqueous solution to the zero osmotic pressure difference concentrator.

2. The method of claim 1, wherein the aqueous solution containing a solute to be concentrated is selected from the group consisting of seawater, brackish water, aqueous solutions of cellular metabolites, and aqueous solutions of reaction products.

3. The method of claim 1, wherein the volume ratio of the draw chamber to the feed chamber of the zero osmotic pressure difference concentrator is 1/10 to 1/100.

4. The method of claim 1, wherein the concentration by the zero osmotic pressure difference concentrator in step (b) is performed in a batch manner or a continuous manner.

5. The method of claim 1, wherein each of the feed chamber and the draw chamber is composed of multiple stages.

6. The method of claim 1, wherein the aqueous solution containing a solute has a pH of 2-13 and a temperature at which water is maintained in liquid state.

7. The method of claim 1, wherein recovery of the solute and water from the aqueous solution concentrated in the zero osmotic pressure difference concentrator is performed by a method selected from the group consisting of a multi-stage flash process, a pervaporation process, a thermal decomposition process, a sulfuric acid process, and a calcium process.

* * * * *